US00PP26474P3

(12) United States Plant Patent
Lavania et al.

(10) Patent No.: US PP26,474 P3
(45) Date of Patent: Mar. 8, 2016

(54) **AUTOTETRAPLOID *VETIVERIA ZIZANIODES* PLANT USEFUL FOR CARBON SEQUESTRATION AND SOIL CONSERVATION NAMED 'CIMAP-KH 40'**

(50) Latin Name: *Vetiveria zizaniodes*
Varietal Denomination: CIMAP-KH 40

(75) Inventors: Umesh Chandra Lavania, Lucknow (IN); Santosh Kumar Rai, Lucknow (IN); Seshu Lavania, Lucknow (IN); Surochita Basu, Lucknow (IN); Basant Kumar Dubey, Lucknow (IN); Ram Ujagir, Lucknow (IN)

(73) Assignee: Council of Scientific and Industrial Research, New Delhi (IN)

( * ) Notice: Subject to any disclaimer, the term of this patent is extended or adjusted under 35 U.S.C. 154(b) by 362 days.

(21) Appl. No.: 13/506,598

(22) Filed: Apr. 30, 2012

(65) Prior Publication Data

US 2012/0278945 P1 Nov. 1, 2012

(30) Foreign Application Priority Data

Apr. 29, 2011 (IN) ..... 1258/DEL/2011

(51) Int. Cl.

| | |
|---|---|
| ***A01H 5/06*** | (2006.01) |
| ***A01H 5/12*** | (2006.01) |
| ***A01H 5/10*** | (2006.01) |

(52) U.S. Cl.
USPC ..... Plt./384
CPC ... *A01H 5/12* (2013.01); *A01H 5/10* (2013.01)

(58) Field of Classification Search
USPC ..... Plt./384
See application file for complete search history.

(56) References Cited

PUBLICATIONS

U.C. Lavania, Enhanced productivity of the essential oil in the artificial autopolyploid of vetiver (*Vetiveria zizanioides* L. Nash), Euphytica 38: 271-276 (1988).*
U.C. Lavania, Enhanced productivity of the essential oil in the artificial autopolyploid of vetiver (*Vetiveria zizaniodes* L. Nash), Euphytica 38: 271-276 (1988).*
U.C. Lavania, Evaluation of an Essential Oil Rich Autotetraploid Cultivar of Vetiver (*Vetiveria zizanioides* (L.) Nash), Journal of Essential Oil Research, vol. 3, Issue 6, CIMAP publication No. 45/91, p. 455-457, 1991.*

* cited by examiner

*Primary Examiner* — Anne Grunberg
(74) *Attorney, Agent, or Firm* — Ladas & Parry LLP

(57) ABSTRACT

The present invention relates to the development of a novel clone of Vetiver [*Vetveria zizaniodes* (L) Nash. syn. *Chrysopogon zizaniodes* (L.) Roberty; family Poaceae], named 'CIMAP-KHUS 40' characterised by somatic chromosome number 4x=40, larger stomata, fast growing deep penetrating roots, and seed infertility disabling its spread as a weed. This clone has unique ISSR and RAPD profiles that serve as DNA-fingerprints, and is developed from a unique diploid plant (2n=20). The invention document details all the pertinent data relating to this clone, its biological features and usefulness, and the method of its development.

3 Drawing Sheets

Figure 1:
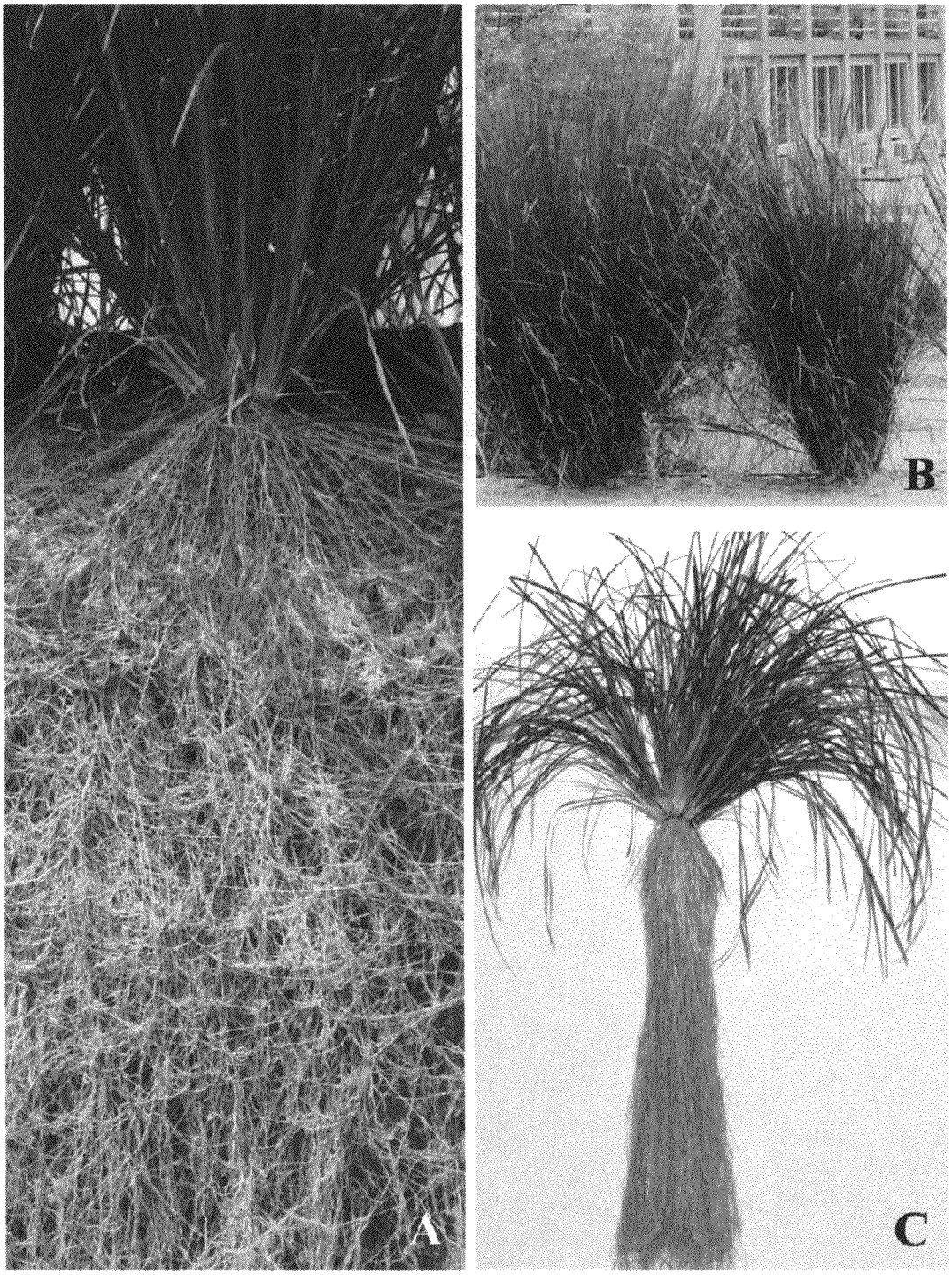

Botanical classification:

Latin name of the genus and species of the plant claimed: Genus: *Vetiveria* (syn. *Chrysopogon*). Species: *zizaniodes.*

Variety denomination: CIMAP-KH 40.

DESCRIPTION

Field of Invention

The present invention relates to the development and utility of a novel seed infertile autotetraploid clone of Vetiver [*Vetveria zizaniodes* (L) Nash. syn. *Chrysopogon zizaniodes* (L.) Roberty; family Poaceae], named CIMAP-KH 40 characterised by somatic chromosome number 4x=40, developed through genomic duplication of a unique diploid clone (2n=20) isolated from a cultivated area. The invention document details all the pertinent data relating to this clone, its biological features and usefulness, and the method of its development.

Background of Invention

The vetiver grass is an important candidate to address current environmental concerns and human well being. This grass traditionally used for extraction of essential oil, has attracted world attention as a natural inexpensive and practical means for its multifarious environmental applications, including conservation and detoxification of degraded soil and water, flood and landslide disaster mitigation (website of vetiver). Lately, Lavania U C and Lavania S (*Curr. Sci.* 97: 618-619, 2009) have proposed a "vetiver grass model" for sequestration of atmospheric carbon into subsoil horizons to mitigate global warming. However, for successful implementation of Vetiver grass for environmental applications it is desirable that such plantations meet the specific environmental objectives without any threat of becoming weedy through seed dispersal and trespassing the target areas. As such, the ideal plant type should have non-seeding habit suitable for eco-friendly plantations.

Vetiver, *Vetiveria zizaniodes* is a perennial densely tufted $C_4$ grass native to India. The grass comprises of prolific clump of tillers, long leaves, erect panicle form of inflorescence and deep penetrating tufted fibrous roots. The spikelets in the panicle appear as pairs of a sessile and pedicellate floret, of which only the former is hermaphrodite producing seeds. The grass can be grown by vegetative propagation through its tillers (slips) as well as through seeds. Owing to profuse seed formation it spreads as a weed, particularly along the river banks and marshy lands. The grass is now grown all across the globe from tropical to Mediterranean climate and can tolerate wide range of temperature and soil conditions. Although, there are no gross morphological differences amongst the vetiver diversity occurring in India but there are distinct karyo-morphologically and reproductively differentiated geographic complexes (Lavania U C *Cytologia* 50:177-185; 1985). The vetiver occurring in north India is profuse flowering and high seed setting (seed germinability upto 50%), but those cultivated in south India are late/low flowering with high pollen sterility and low seed setting. However, the latter when grown under north Indian conditions (i.e. in Lucknow) show good seed-set and seed germinability of 10-15%. Although, there are unsubstantiated reports about non-seed forming vetiver and flowering of vetiver as late as three years after plantation in certain parts of the globe, but as said above even the low seed forming vetiver from south India when grown in north India does flower regularly and form fertile seeds. As such, no non-seeding vetiver is yet available in true sense that could be safely used for ecological plantations.

The autotetraploid clone of vetiver, named ('CIMAP-KH 40') which is seed infertile has been developed from a unique diploid plant that had low seed fertility and fast growing roots. The above said diploid source plant was isolated from the road-side plant populations of Vetiver inhabiting plains of the state of the Uttar Pradesh in India where this plant occurs in wild, and is also cultivated for its aromatic roots and extraction of essential oil. The diploid source plant was subjected to artificial induction of polyploidy to realise its clonal autotetraploid 'CIMAP-KH 40' that exhibited further reduction in seed fertility i.e. stunted seeds with zero germinability, and enhanced biomass/growth characteristics. Thus 'CIMAP-KH 40' offers utilitarian opportunities for controlled plantations of vetiver to mitigate global warming and soil degradation without posing any threat of becoming weedy.

Other General References

1. Manual: *Factual tips about Vetiver grass.* ISBN 974-7772-49-3. Office of the Royal Development Projects Board., Bangkok, Thailand, pp. 103
2. National Research Council (1993) *Vetiver grass: a thin green line against erosion.* National Academy Press, Washington, D.C., pp. 169.

The main object of the present invention is to develop a clone of vetiver that has non-seeding (seed infertile) characteristics no that it does not spread (is non-invasive) to undesired destinations, and could be conveniently grown under controlled plantations without becoming weedy, and has deep penetrating fast growing roots for best utilization for its multifarious environmental applications.

SUMMARY OF THE INVENTION

The present invention relates to the development and utility of a new and distinct sexually infertile autotetraploid plant of Vetiver, *Vetveria zizaniodes* (L.) Nash. syn. *Chrysopogon zizaniodes* (L.) Roberty; family Poaceae, named 'CIMAP-KH 40' characterised by somatic chromosome number 4x=40, developed through genomic duplication of a unique diploid clone (2n=20) isolated from a wild population inhabiting the cultivated area in the state of Uttar Pradesh in India. The invention document details all the pertinent data relating to this clone, its biological features and usefulness, and the method of its development.

BRIEF DESCRIPTION OF THE ACCOMPANYING DRAWINGS

FIG. 1: Exo-morphology of clone ('CIMAP-KH 40'). A. Root growth pattern, B. Late flowering and fast growth in the autotetraploid clone (left) compared to south Indian clone (right) grown at CIMAP, Lucknow, C. The autotetraploid clone showing plant growth and shoot: root ratio at three month growth stage. Dates of the photographs taken: A. 26 May 2010, B. 16 Aug. 2009, C. 4 Mar. 2010.

FIG. 2: Somatic chromosomes, stomata and DNA fingerprints of clone ('CIMAP-KH 40'). A. Somatic chromosomes=40, B-C Stomata—Larger stomata in the autotetraploid (B) and normal size stomata in the source diploid (C), D-E. DNA fingerprints based on: A. ISSR markers, B. RAPD markers.

Figure 3:
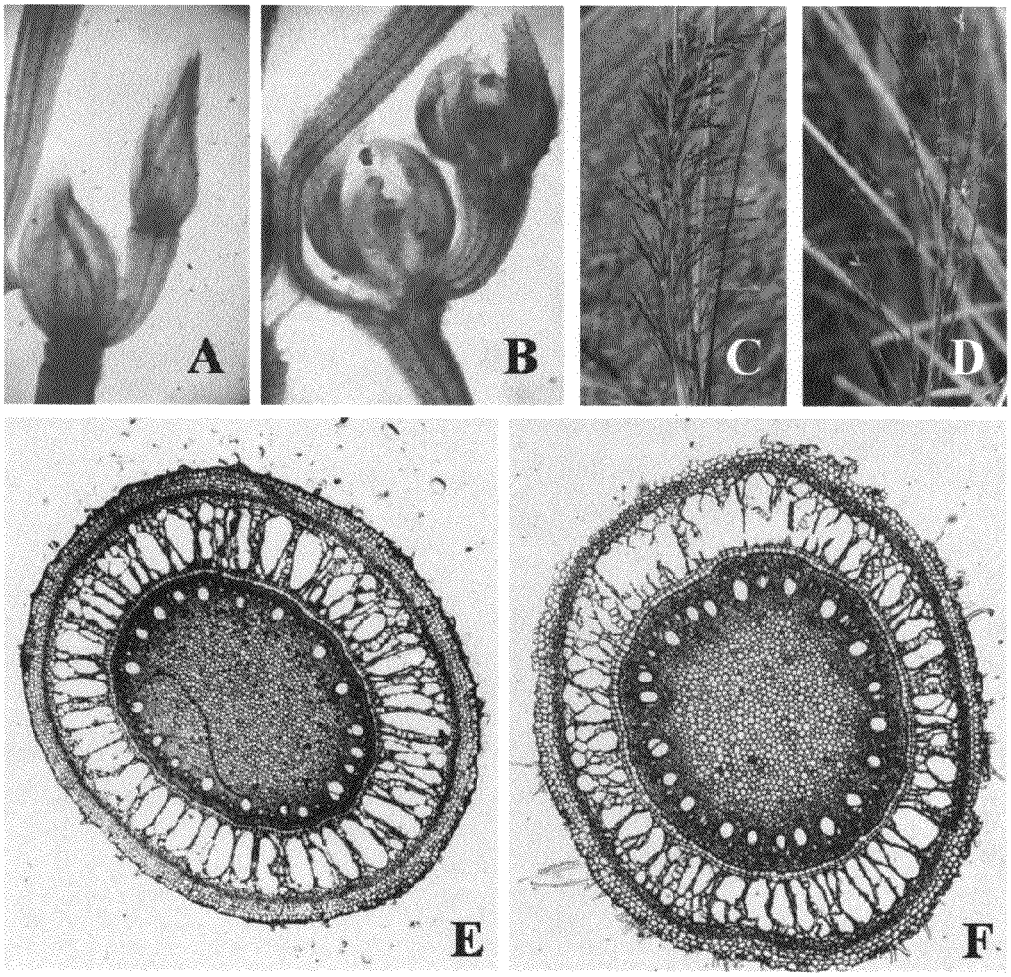

FIG. 3: Comparative view of the spikelet showing sessile and pedicellate florets, Inflorescence axis and TS of the root in the progenitor diploid (A, C, E) and corresponding autotetraploid clone ('CIMAP-KH 40') (B, D, F). Note, enlarged floret size, lax inflorescence and larger vascular cylinder in the root of the autotetraploid clone.

DETAILED BOTANICAL DESCRIPTION

Breeding History

Polyploidy is often accompanied by conspicuous changes in morphology and bio-efficiency consummated through increased cell size and enhanced cell surface related biological activities, but show reduced reproductive fitness owing to disturbances in meiotic behaviour. Polyploid plants often develop larger plant organs, and thus become ecologically and/or reproductively altered compared to their diploid progenitors. Polyploidy often causes disturbances in meiotic behaviour leading to imbalanced and sterile gametes thus limiting seed fertility. As such, polyploidy could be an important means to enhance biological potential of plants where plant biomass/body size is the target for improvement and seed production is dispensable. Therefore, artificial polyploidy is considered as an appropriate means to realise non-seeding/seed sterility/reduced seed set to mitigate the spread of target plants to undesired destinations through abiotic and biotic means of seed dispersal, as well as to improve the target plant for its growth behaviour and vegetative fitness.

In vetiver, polyploidy has been attempted earlier using young seedlings (Lavania U C *Euphytica* 37: 271-276, 1988; Lavinia U C. Base S and Lavinia S (2006) Proc. 4$^{th}$ International Conf on Vetiver, Caracas, Venezuela). Whereas, the polyploids thus realised exhibited reduction in seed fertility, but there was no control on the genetic fidelity of heterozygous diploid source because the seedlings used for polyploidy induction had a segregating genetic make-up that is different from the source diploids, and also the seedlings inherit the seed forming potential of the progenitor diploid source. Therefore, in the present investigation for polyploidy induction the target material used was not the seedlings, but a unique diploid clone isolated from a cultivated area that had desirable characteristics with very low seed fertility.

Method of Development of the Clone ('CIMAP-KH 40')

Administration of colchicine to growing tissues facilitates induction of polyploidy in plants. Whereas, the induction of polyploidy is relatively easy in the dicot plants because of easy accessibility of apical meristem, but induction of polyploidy is experimentally quite difficult in grasses on account of difficult to access the basal meristem that lay deep seated beneath the leaf base.

In order to realise non-seedy nature and fast growing feature it is very important to identify the target diploid plant. Several fast growing plants identified from diverse cultivated areas in the plains of the Uttar Pradesh India were collected and grown at the experimental farm of the Central Institute of Medicinal and aromatic plants, Lucknow, India, and screened for late/low flowering and low seed fertility. One fast growing plant that has low seed fertility (seed germinability as low as 3%) was isolated and targeted for the induction of polyploidy. The lateral shoot buds near the leaf base from the fast growing tillers were exposed by removing the cover leaf. 100 numbers of such tillers were immersed in 0.1% aqueous solution of Colchicine prepared in 2% DMSO (Dimethyl Sulphoxide) for 07 hours at ~25° C. followed by thorough washing in running water. Only the lower 8 cm portion of the tillers that had axillary buds was kept immersed in colchicine solution. After washing, the treated tillers were given overnight recovery period from colchicine shock in 1X Hoagland's solution, and then planted in the experimental field followed by optimum cultural care. The leaves from lateral tillers emerging from the colchicine treated tillers were examined for the size of stomata in the epidermal peel from the abaxial side of the leaf. Only one leaf-shoot emerging from one of the treated tillers showed linear streaks of larger stomata in the central region of the leaves. This tiller was scored-out, its vegetative progenies were screened cytologically for polyploid chromosome number and uniform occurrence of larger stomata in the entire leaf. Cytologically stable polyploid clone was further allowed to undergo six successive rounds of tillerring to ensure polyploid purity and stability. The autotetraploid clone was subsequently multiplied by vegetative propagation through slips (i.e. vegetative tillers proliferating from the basal part of shoot that get rooted after plantation) at the institute's experimental farm at Lucknow for further evaluation.

DETAILED BOTANICAL DESCRIPTION

Uniformity and Stability

After ascertaining uniformity and genetic stability for six successive rounds of vegetative tillerring, the autotetraploid clone was multiplied through its slips. The polyploid clone is genetically pure and cytologically stable for its autotetraploid nature (4X=40). Sufficient quantity of planting material could be conveniently generated by asexual propagation through slips for plantation purpose.

Seed Fertility

Compared to all other fast growing clones, the present autotetraploid clone ('CIMAP-KH 40') exhibits delayed flowering (a delay of over one month), lax and reduced panicle and seed fertility almost zero (i.e. no seed germination under laboratory conditions) compared to its progenitor diploid clone that show 3% germination, and other clones showing seed germination ranging from 10-50%.

In fact, the ovule borne in the hermaphrodite sessile flower in CIMAP-KH 40 slender exhibiting stunted growth and the 'so called seed' thus formed resemble solid carpel lacking true seed like characteristics and reproductive potential.

It may be mentioned that Lucknow climate is otherwise most suitable climate for fertile seed formation in Vetiver since even the low seed forming vetiver from south India, and clones from Thailand does form fertile seeds under Lucknow conditions. Therefore, it is believed that the autotetraploid clone ('CIMAP-KH 40') would not form fertile seeds when grown in other parts of the globe.

Growth Potential

Under optimum field conditions with sandy soil the initial root emerging from the single tiller reaches upto the length of 90 cms in one month, and a 130 cms long tuft of 160 nos. of roots and a clump of 40 nos. of tillers after three months. In six months this tufted root system grows up-to 250 cms and shoot: root length ratio of 1:2 (compared to 1:1.5 in the progenitor diploid source). After three months, the length of root tuft is 100 cms in the progenitor diploid and 80-100 cms in other varieties. The roots could grow through the soil hardpan crust as well.

Carbon Sequestration Potential of the Auto-Tetraploid Clone

When grown in sandy soil with optimum cultural care the clone ('CIMAP-KH 40') is capable of producing 1.02 kg. of dry root biomass (of which 43% is the carbon content) from one square meter area with single slips planted at 40 cms×40 cms plant-to-row distance after six months, compared to 950 g of dry root biomass in the progenitor diploid and 700 to 950 gms in other varieties. Owing to the exponential root growth, this root biomass yield is likely to double after one year, with an estimated carbon sequestration potential of 860 g/square meter/year.

Characterization of the Auto-Tetraploid Clone

Genus: *Vetiveria* (syn. *Chrysopogon*).

Species: *zizaniodes*.

Family: Poaceae.

Common name: Vetiver (in Hindi in India: KHUS).

Cultivar name: ('CIMAP-KH 40').

The autotetraploid clone ('CIMAP-KH 40') is fast growing and late flowering (FIG. 1), characterised by its somatic chromosome number 4x =40, larger stomata and unique DNA-fingerprints (FIG. 2), and enlarged floral organs and thick roots (FIG. 3). Further details are as under:

Morphometric Description of the Autotetraploid Clone 'CIMAP-KH 40'

General morphology: Clumpy with long erect leaves, capable of rattooning and aerial branching.

Growth habit: Perennial, profuse synchronous whorly tiller pattern. Under Lucknow conditions the clone ('CIMAP-KH 40') flowers after eight months of planting done in the month of March, i.e. a delay of 30-45 days compared to other genetic stocks, its root growth is faster by at least 1,3 times and roots/vascular cylinder is thicker by at least 15% compared to existing varieties.

Plant height: After 180 days of planting: 1.45 meter, inflorescence stalk length (i.e. 240 days after planting); 2.0 meters.

Culm and leaf: Tiny shoot (culm) hidden in the leaf sheath with 6-8 leaves per tiller sprouting from the bottom of the clump. Internode—pithy.

Leaf: Dark green in color (Royal Horticultural Society London, 5$^{th}$ Edition 2007 RHS color N137-A color chart green-group N137-A, Upper—RHS color 138B), lower surface of leaf is smooth and upper waxy hairy texture, ligule narrow hairy rim, auricle absent, leaf sheath terete, leaf blade linear), smooth and waxy texture, Leaf blade is broad, width at leaf base=2.6 cms. (compared to 2.2 cms. in the progenitor diploid, and 1.35 cms in south Indian varieties and 1.6 to 2.1 cms in north Indian varieties), thick leaves—thickness of the midrib measured at three cms above the leaf base=2.2 mm (compared to 1.5 mm in the diploid progenitor, 1.0 mm in south Indian varieties and 1.3 to 1.5 mm in the north Indian varieties), the adaxial surface of the two halves of the leaf blade are inwardly folded at the base but gradually open towards apical side, leaf apex acute, petiole length (outer three leaves)=120-145 cms., with their average leaf area 180 $cms^2$ (compared to 160 $cms^2$ in source diploid). The average size of stomata (both guard cells)=935 $\mu m^2$ with a stomatal frequency of 77 stomata/$mm^2$ of leaf surface compared to 491 $\mu m^2$ with a stomata frequency of 144 stomata/$mm^2$ in the diploid clone, respectively. It may be pertinent to mention here that the stomata of the progenitor diploid plant type used in this investigation are relatively smaller in size by 10% compared to other diploid cultivars in vogue, and the same is correspondingly reflected in the autotetraploid clone ('CIMAP-KH 40').

Peduncle: The inflorescence bearing peduncle and culm combined together reach upto two meter long, of which peduncle is 50-70 cms long in 'CIMAP-KH 40' compared 60-80 cms in the parent diploid. The ⅓ top part of the peduncle is flower bearing.

Inflorescence: Panicle type, purplish (RHS color N79-C), lax inflorescence and enlarged floret size with stalk and panicle together reaching upto two meter long.

Inflorescence and panicle: Inflorescence is a panicle with lax inflorescence and enlarged floret size. The flower bearing part of the inflorescence mother axis is 20-25 cm long with 7-10 internodes; each node with a whorl of 5-8 spikes and each spike with pairs of 4-6 spikelets raceme, as compared to 27-35 cm long mother axis with 10-18 internodes with a whorl of 8-12 spike and each spike with pairs of 5-9 spikelets raceme in the progenitor diploid. Each panicle comprises 400-600 flowers in CIMAP-KH40, compared to 600-1000 in the parent diploid. Inflorescence is persistent that lasts till maturity.

Flower: Floral axis Purplish color (RHS color N79-C), flowers are borne as pairs of male pedicellate and hermaphrodite sessile spikelets on the spike rachilla. and initial floret size of w×l=0.8×1.7 mm pedicellate flower and 1.4×2.8 mm sessile flower compared to 0.6×1.2 mm pedicellate and 1.0×1.9 mm sessile flower in the progenitor diploid. Number of stamens in a flower=3, bifid feathery stigma.

Ovule: Ovule is slender compared to standard; measuring w×l=0.3×0.65 mm in source diploid and 0.4×0.75 mm in the standard diploid; and 0.45×0.9 mm in 'CIMAP-KH4' compared 0.6×10.5 mm in another tetraploid, showing stunted development of ovule in the CIMAP-KH 40 as well as its diploid parent. Such stunted ovular growth attendant in CIMAP-KH40 and its progenitor diploid, is also reflected in the stunted seeds.

Glumes:

*Sessile spikelet*.—Lower glume (RHS color — Yellow-Green group 144D with base and spines Red-Purple Group 61 B) coriaceous, narrowly ovate, 4.8-5.2×1.3-1.7 mm, margins inflexed, 5-nerved, keels spinulose, apex subacuate; Upper glume (RHS color — Yellow-Green group 144 D with base and spines Red-Purple Group 61B) hyaline, broadly ellliptic-oblong, 4.9-5.1×1.9-2.0 mm, 3-nerved, keel covered with scabrid hairs, margins ciliate, apex acute.

Lemma:

*Sessile spikelet*.—Lower lemma (RHS color — White group NN155) membranous, narrowly obovate, 4.5-4.8×1.5-1.6 mm, glabrous, margin ciliate, apex acute; Upper lemma (RHS color — White group NN155) hyaline, oblong, 4.0-4.2×1.4-1.6 mm, apex acute.

Palea:

*Sessile spikelet*.—RHS color — White Group NN155, hyaline, oblong, 2.83.4×1.0-1.2 mm, apex rounded.

Seed set: Infertile seeds resembling solid carpel virtually with no seed germination.

Oil content: 1.5% in fresh roots (with 45% moisture) after 15 hrs of hydrodistillation at 10 months of growth.

Root diameter (at the base of main root): 2.3 mm compared to 2.0 mm in the progenitor diploid, and 1.4 to 2.0 mm in other varieties); vascular cylinder 1.4 mm in diameter compared to 1.2 mm in the progenitor diploid and 0.9 to 1.2 mm in other varieties.

Root yield: (Dry matter)/sq. meter at 180 days=1.02 kg.

Shoot yield: (Culm/leaf dry matter)/sq. meter at 180 days=1.54 kg.

Carbon content: In the roots: 43%, in shoots: 37%.

Estimated carbon sequestration potential into subsoil/year/square meter: 860 g.

As compared to other Vetiver varieties in India, this ('CIMAP-KH 40') clone is distinct in respect of combination of characters like infertile seeds, lax inflorescence with enlarged floret size, deep penetrating interwoven mesh of roots with faster growth by at least 1.3 times and shoot:root length ratio of 1:2, roots/vascular cylinder thicker by at least 15% as compared to existing varieties, root diameter at the base of roots at least 2.3 mm as compared to 2.0 mm in the progenitor diploid, and 1.4 to 2.0 mm in other varieties, capable of producing 1.02 kg. of dry root biomass (of which 43% is the carbon content) from one square meter area with single slips planted at 40 cms×40 cms plant-to-row distance after six months, broad leaf blade with width at leaf base at least 2.6 cms as compared to 2.2 cms in the progenitor diploid, and 1.35 to 2.1. cms in other varieties, thick leaves with midrib thickening measured at three cms above the leaf base measures about 2.2 mm as compared to 1.5 mm in the parent and 1.0 mm to 1.5 mm in other varieties, larger stomata size of both guard cells measuring at least 935 $\mu m^2$ and having frequency of about 77 stomata/$mm^2$ of abaxial side leaf surface area compared to 491 μm2 with a stomatal frequency of 144 stomata/ mm2 in the diploid parent, respectively.

Comparison of 'CIMAP-KH 40' with the other tetraploid variety 'Sugandha': 'CIMAP-KH40' is an induced clonal tetraploid which is late and low flowering plant that flowers after eight months of plantation producing only infertile seeds (i.e. zero germinability) and has been developed from a preselcctcd low seed fertility diploid progenitor clone (having seed germinability only up to 3%), whereas, 'Sugandha' is an early and high flowering tetraploid that flowers after six months of plantation and produces fertile seeds that have over 30% seed germination, and has been developed from seeds obtained from a high seed forming (having 50% seed germinability) heterozygous progenitor diploid. As such 'Sugandha' is not suitable for ecological plantation since this may become weedy because of its seed forming potential. Further, 'CIMAP-KH 40' has fast growing high biomass producing thicker roots (root diameter 2.3 mm at the base of main root compared 2.14 mm thick roots in 'Sugandha'). The fresh roots of 'CIMAP-KH 40' can yield 1.5% (v/w) essential oil from its roots harvested just after 10 months of plantation, however 'Sugandha' would require longer period of plantation (18 months) to obtain same concentration of essential oil.

The selected variety was christened as ('CIMAP-KH 40') and grown for six consecutive rounds to study its genetic stability, growth and morphological characteristics. ('CIMAP-KH 40') maintained uniformity in its growth and morphological characteristics.

The Main Advantages of the Present Invention and Utility of the Invented Clone

1. The autotetraploid clone ('CIMAP-KH 40') offers enhanced opportunities for its utlization in mitigating global warming through photosynthetic capture of atmospheric carbon dioxide and its long-term sequestration in sub-soil horizons through its fast growing deep penetrating roots.
2. The said autotetraploid clone offers enhanced opportunities for its utilization in mitigating soil degradation owing to its mesh forming soil binding fast growing deep penetrating roots.
3. The said autotetraploid clone is seed infertile, therefore it does not pose any problem of becoming weedy due to seed dispersal and is ideally suited for controlled plantations.
4. The said autotetraploid clone could be easily grown vegetatively through tiller propagation, and as such the genetic fidelity of the clone would be maintained under plantation.
5. The said autotetraploid clone promises high biomass of deep penetrating roots that go far beyond the plough layer, thereby facilitating higher carbon sequestration into subsoil horizons.
6. The said autotetraploid clone promises R & D opportunities for realizing chromosomal and genetic manipulation through its utilization in intercrossing/in vitro manipulation for value addition.
7. The said clone offers all other advantages offered by the vetiver grass for its multifarious uses with enhanced potential owing to its higher biomass (i.e. shoot and root).

SEQUENCE LISTING

```
<160> NUMBER OF SEQ ID NOS: 20

<210> SEQ ID NO 1
<211> LENGTH: 17
<212> TYPE: DNA
<213> ORGANISM: ARTIFICIAL SEQUENCE
<220> FEATURE:
<223> OTHER INFORMATION: ISSR PRIMER UBC 807

<400> SEQUENCE: 1

agagagagag agagagt                                                    17


<210> SEQ ID NO 2
<211> LENGTH: 17
<212> TYPE: DNA
<213> ORGANISM: ARTIFICIAL SEQUENCE
<220> FEATURE:
<223> OTHER INFORMATION: ISSR PRIMER UBC 810

<400> SEQUENCE: 2

gagagagaga gagagat                                                    17


<210> SEQ ID NO 3
<211> LENGTH: 17
<212> TYPE: DNA
<213> ORGANISM: ARTIFICIAL SEQUENCE
<220> FEATURE:
<223> OTHER INFORMATION: ISSR PRIMER UBC 811

<400> SEQUENCE: 3

gagagagaga gagagac                                                    17


<210> SEQ ID NO 4
<211> LENGTH: 17
<212> TYPE: DNA
<213> ORGANISM: ARTIFICIAL SEQUENCE
<220> FEATURE:
<223> OTHER INFORMATION: ISSR PRIMER UBC 812

<400> SEQUENCE: 4

gagagagaga gagagaa                                                    17


<210> SEQ ID NO 5
<211> LENGTH: 17
<212> TYPE: DNA
```

-continued

<213> ORGANISM: ARTIFICIAL SEQUENCE
<220> FEATURE:
<223> OTHER INFORMATION: ISSR PRIMER UBC 814

<400> SEQUENCE: 5 ctctctctct ctctcta 17

<210> SEQ ID NO 6
<211> LENGTH: 17
<212> TYPE: DNA
<213> ORGANISM: ARTIFICIAL SEQUENCE
<220> FEATURE:
<223> OTHER INFORMATION: ISSR PRIMER UBC 818

<400> SEQUENCE: 6 cacacacaca cacacag 17

<210> SEQ ID NO 7
<211> LENGTH: 17
<212> TYPE: DNA
<213> ORGANISM: ARTIFICIAL SEQUENCE
<220> FEATURE:
<223> OTHER INFORMATION: ISSR PRIMER UBC 823

<400> SEQUENCE: 7 tctctctctc tctctcc 17

<210> SEQ ID NO 8
<211> LENGTH: 17
<212> TYPE: DNA
<213> ORGANISM: ARTIFICIAL SEQUENCE
<220> FEATURE:
<223> OTHER INFORMATION: ISSR PRIMER UBC 825

<400> SEQUENCE: 8 acacacacac acacact 17

<210> SEQ ID NO 9
<211> LENGTH: 17
<212> TYPE: DNA
<213> ORGANISM: ARTIFICIAL SEQUENCE
<220> FEATURE:
<223> OTHER INFORMATION: ISSR PRIMER UBC 826

<400> SEQUENCE: 9 acacacacac acacacc 17

<210> SEQ ID NO 10
<211> LENGTH: 17
<212> TYPE: DNA
<213> ORGANISM: ARTIFICIAL SEQUENCE
<220> FEATURE:
<223> OTHER INFORMATION: ISSR PRIMER UBC 828

<400> SEQUENCE: 10 tgtgtgtgtg tgtgtga 17

<210> SEQ ID NO 11
<211> LENGTH: 10
<212> TYPE: DNA
<213> ORGANISM: ARTIFICIAL SEQUENCE
<220> FEATURE:
<223> OTHER INFORMATION: RAPD PRIMER OPJ 6

<400> SEQUENCE: 11

-continued tcgttccgca 10

<210> SEQ ID NO 12
<211> LENGTH: 10
<212> TYPE: DNA
<213> ORGANISM: ARTIFICIAL SEQUENCE
<220> FEATURE:
<223> OTHER INFORMATION: RAPD PRIMER OPJ 9

<400> SEQUENCE: 12 tgagcctcac 10

<210> SEQ ID NO 13
<211> LENGTH: 10
<212> TYPE: DNA
<213> ORGANISM: ARTIFICIAL SEQUENCE
<220> FEATURE:
<223> OTHER INFORMATION: RAPD PRIMER OPJ 10

<400> SEQUENCE: 13 aagcccgagg 10

<210> SEQ ID NO 14
<211> LENGTH: 10
<212> TYPE: DNA
<213> ORGANISM: ARTIFICIAL SEQUENCE
<220> FEATURE:
<223> OTHER INFORMATION: RAPD PRIMER OPJ 12

<400> SEQUENCE: 14 gtcccgtggt 10

<210> SEQ ID NO 15
<211> LENGTH: 10
<212> TYPE: DNA
<213> ORGANISM: ARTIFICIAL SEQUENCE
<220> FEATURE:
<223> OTHER INFORMATION: RAPD PRIMER OPJ 13

<400> SEQUENCE: 15 ccacactacc 10

<210> SEQ ID NO 16
<211> LENGTH: 10
<212> TYPE: DNA
<213> ORGANISM: ARTIFICIAL SEQUENCE
<220> FEATURE:
<223> OTHER INFORMATION: RAPD PRIMER OPJ 14

<400> SEQUENCE: 16 cacccggatg 10

<210> SEQ ID NO 17
<211> LENGTH: 10
<212> TYPE: DNA
<213> ORGANISM: ARTIFICIAL SEQUENCE
<220> FEATURE:
<223> OTHER INFORMATION: RAPD PRIMER OPJ 15

<400> SEQUENCE: 17 tgtagcaggg 10

<210> SEQ ID NO 18
<211> LENGTH: 10
<212> TYPE: DNA

-continued

```
<213> ORGANISM: ARTIFICIAL SEQUENCE
<220> FEATURE:
<223> OTHER INFORMATION: RAPD PRIMER OPJ 16

<400> SEQUENCE: 18

ctgcttaggg                                                          10


<210> SEQ ID NO 19
<211> LENGTH: 10
<212> TYPE: DNA
<213> ORGANISM: ARTIFICIAL SEQUENCE
<220> FEATURE:
<223> OTHER INFORMATION: RAPD PRIMER OPJ 17

<400> SEQUENCE: 19

acgccagttc                                                          10


<210> SEQ ID NO 20
<211> LENGTH: 10
<212> TYPE: DNA
<213> ORGANISM: ARTIFICIAL SEQUENCE
<220> FEATURE:
<223> OTHER INFORMATION: RAPD PRIMER OPJ 18

<400> SEQUENCE: 20

tggtcgcaga                                                          10
```

What is claimed is:

1. A new and distinct variety of an autotetraploid plant named CIMAP-KH 40 as illustrated and described herein.

* * * * *

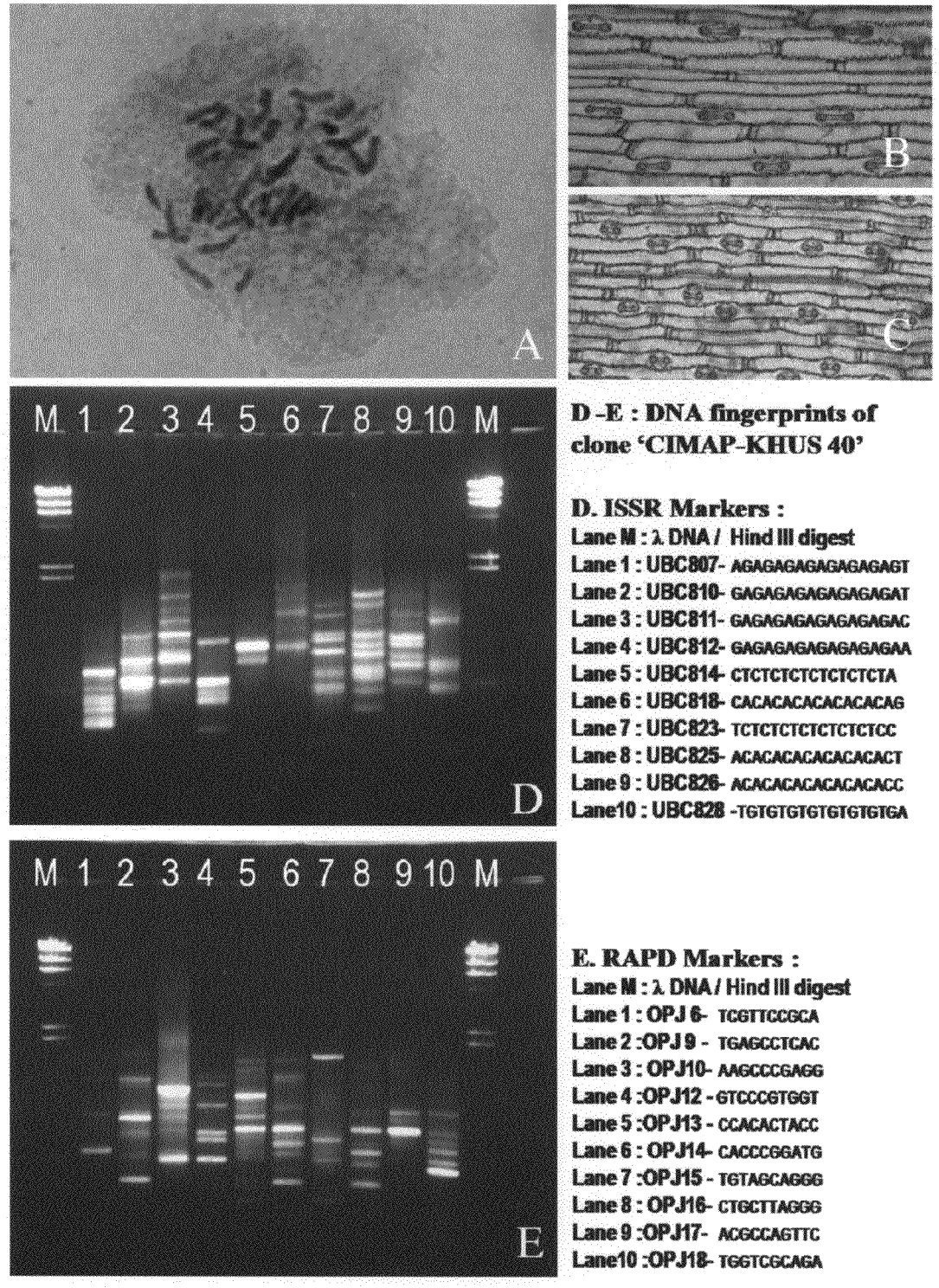

D -E : DNA fingerprints of clone 'CIMAP-KHUS 40'

D. ISSR Markers :

Lane M : λ DNA / Hind III digest
Lane 1 : UBC807- AGAGAGAGAGAGAGAGT
Lane 2 : UBC810- GAGAGAGAGAGAGAGAT
Lane 3 : UBC811- GAGAGAGAGAGAGAGAC
Lane 4 : UBC812- GAGAGAGAGAGAGAGAA
Lane 5 : UBC814- CTCTCTCTCTCTCTCTA
Lane 6 : UBC818- CACACACACACACACAG
Lane 7 : UBC823- TCTCTCTCTCTCTCTCC
Lane 8 : UBC825- ACACACACACACACACT
Lane 9 : UBC826- ACACACACACACACACC
Lane10 : UBC828 -TGTGTGTGTGTGTGTGA

E. RAPD Markers :

Lane M : λ DNA / Hind III digest
Lane 1 : OPJ 6- TCGTTCCGCA
Lane 2 :OPJ 9 - TGAGCCTCAC
Lane 3 : OPJ10- AAGCCCGAGG
Lane 4 :OPJ12 - GTCCCGTGGT
Lane 5 :OPJ13 - CCACACTACC
Lane 6 : OPJ14- CACCCGGATG
Lane 7 :OPJ15 - TGTAGCAGGG
Lane 8 : OPJ16- CTGCTTAGGG
Lane 9 :OPJ17- ACGCCAGTTC
Lane10 :OPJ18- TGGTCGCAGA

Figure 2